United States Patent [19]
Tanaka et al.

[11] Patent Number: 6,024,922
[45] Date of Patent: Feb. 15, 2000

[54] METHOD OF CONTROLLING AN OXYGEN ANALYZER OF THE HERSCH GALVANIC TYPE

[75] Inventors: Yoshiyasu Tanaka; Yoshiro Matsumoto, both of Funabashi, Japan

[73] Assignee: Osaka Sanso Kogyo Ltd., Osaka, Japan

[21] Appl. No.: 08/682,607

[22] PCT Filed: Jan. 26, 1994

[86] PCT No.: PCT/JP94/00102

§ 371 Date: Jul. 25, 1996

§ 102(e) Date: Jul. 25, 1996

[87] PCT Pub. No.: WO95/20755

PCT Pub. Date: Aug. 3, 1995

[51] Int. Cl.$^7$ .................................................. G01N 27/30
[52] U.S. Cl. ..................................... 422/82.04; 422/82.13; 422/83; 422/98; 422/50; 204/406
[58] Field of Search ........................... 73/865.9, 23, 198, 73/714; 98/1.5

[56] References Cited

U.S. PATENT DOCUMENTS

| | | | |
|---|---|---|---|
| 3,698,384 | 10/1972 | Jones | 128/2.07 |
| 3,760,831 | 9/1973 | Colvin | 137/117 |
| 3,933,593 | 1/1976 | Sternberg | 195/103.5 |
| 4,657,737 | 4/1987 | Kampelmuhler | 422/94 |
| 4,973,395 | 11/1990 | Mayer et al. | 204/406 |
| 5,312,761 | 5/1994 | Suzuki et al. | 436/136 |

FOREIGN PATENT DOCUMENTS 047434   3/1982   European Pat. Off. .

OTHER PUBLICATIONS

"Testing Methods for Determination of Trace Components in Diluent Gas and Zero Gas"; Japanese Industrial Standard JIS K 0225—1990.
Hersch/Osaka Oxygen—PPB Oxygen Analyzer, MKIV/Y; Galvanic–cell Type, Osaka Sanso Kogyo Ltd., dated Sep. 1, 1993.
Hersch/Osaka Oxygen—MKIV/S, Trace Oxygen Gas Analyzer, Osaka Sanso Koygo, Ltd., dated Aug. 1, 1993.

*Primary Examiner*—Laurie Scheiner
*Assistant Examiner*—J. S. Parkin
*Attorney, Agent, or Firm*—Roylance, Abrams, Berdo & Goodman, L.L.P.

[57] ABSTRACT

The claimed invention provides an improved oxygen analyzer of the Hersch galvanic type that is suitable for measuring oxygen concentrations of 1 part per million (ppm) or less in a feed gas, as well as, methods of regulating said analyzer. Modifications have been made to the instrument, or its attendant supporting structures, that reduce or eliminate problems associated with the back flow of gas due to pressure differences between pipes for entrance and egress gases, problems associated with dead zones in the apparatus, or problems associated with dissolved oxygen present in water supplied to the detector. These problems have been addressed by modifying the instrument and its attendant structures, inter alia, to include a bypass pipe coupling between a pipe for gas supply to a detector and a pipe at gas outlet, including a check valve halfway between said bypass coupling, and providing means for detecting the pressure differential between a gas supply pipe and gas outlet pipe. Methods for regulating the flow of atmospheric oxygen into the analyzer, regulating the water level in the analyzer, and performing automatic zero and gain adjustments are also provided.

7 Claims, 3 Drawing Sheets

METHOD OF CONTROLLING AN OXYGEN ANALYZER OF THE HERSCH GALVANIC TYPE

TECHNICAL FIELD

This invention relates to an oxygen analyzer suitable for use in the oxygen analysis of gases containing very small amounts of oxygen.

BACKGROUND ART

With the increasing scale of integration of semiconductor circuits, as well as the advances in the technology of ultrahigh precision working, it has become necessary to keep surveillance of the fabrication process, particularly for the oxygen concentration of the process gas which need be monitored over the range from the ppb to sub-ppb level. In such precision measurements, even the oxygen analyzers that have heretofore been used without any problems are found to cause various problems and need be improved.

Among the problems that need be dealt with are that of back flow due to the pressure difference between a pipe for entrance gas to the detector and a pipe for exit gas, the problem of back diffusion of aerial oxygen from the pipe exit gas, the problem due to the dead zones in the apparatus and, further, the problem of dissolved oxygen in the water to be additionally supplied to the detector. As typified by these problems, it has been found that the results of measurements are affected by the presence of such small amounts of oxygen as have been insignificant to the conventional oxygen analyzers.

The present invention has been accomplished with a view to meeting these rigorous requirements. In order to enable precise measurements, the present inventors searched for certain factors of variations ascribable to the analyzer, located the causes of such variations and have proposed effective countermeasures. Thus, the problems to be solved by the invention are novel ones that have been first identified by the present inventors. It should be noted that the term "very small amounts" as used with oxygen in the specification refers to concentrations of no more than about 1 ppm.

DISCLOSURE OF THE INVENTION

The oxygen analyzer of the invention is suitable for use in the oxygen analysis of gases containing very small amounts of oxygen and it features various improvements typified by a bypass pipe coupling between a pipe for gas supply to a detector and a pipe at gas outlet, a check valve provided halfway said bypass pipe and means for detecting the pressure difference between said gas supply pipe and said gas outlet pipe.

It should also be noted that the oxygen analyzer to be used in the invention is of a Hersch galvanic type and contains an aqueous solution (electrolyte) of a specified concentration range within a detector; the operating principle of the analyzer is such that the oxygen in a feed gas undergoes chemical reaction with the water in the electrolyte, whereby an electric current flows between electrodes in the electrolyte to permit the measurement of oxygen concentration. It should further be noted that the detector is capable of being supplied with a gas to be measured, a zero gas and a gain gas and these feed gases can be switched from one type to another by suitable means such as a valve. For the parts that are not particularly mentioned in the specification, any parts of and means in known oxygen analyzers may be applied.

BEST MODE FOR CARRYING OUT THE INVENTION

The inventions recited in the respective claims are hereunder described seriatim.

The invention recited in claim 1 relates to an oxygen analyzer suitable for use in the oxygen analysis of gases containing very small amounts of oxygen and it is characterized by having a bypass pipe coupling between a pipe for gas supply to a detector and a pipe at gas outlet, a check valve provided halfway said bypass pipe, and means for detecting the pressure difference between said gas supply pipe and said gas outlet pipe.

Figure 1:
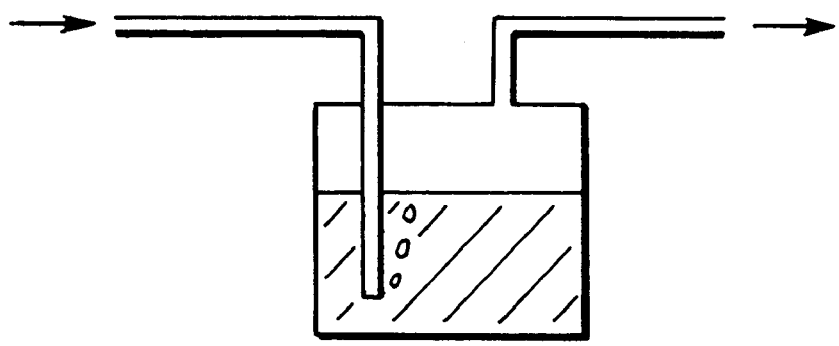
FIG. 1 is a diagram showing a prior art oxygen analyzer having no bypass line.

In many conventional cases, there have been provided no means for preventing the electrolyte in the detector from flowing back to the gas supply pipe (see FIG. 1). The only measure that has been taken is no more than providing a check valve. A back flow of the electrolyte will naturally cause variations in the result of analysis and hence is not preferred from a measurement viewpoint. Even if a check valve is provided as a countermeasure, the presence of back pressure or capillarity makes it difficult to achieve complete prevention of the back flow. In addition, due to a structural feature of the valve that it has a large internal space, there is produced a large gas reservoir to increase the amount of the gas that has been present before the gas to be measured and which hence need be purged out of the detector. This has eventually caused the problem of deteriorated response in analysis.

Figure 2:
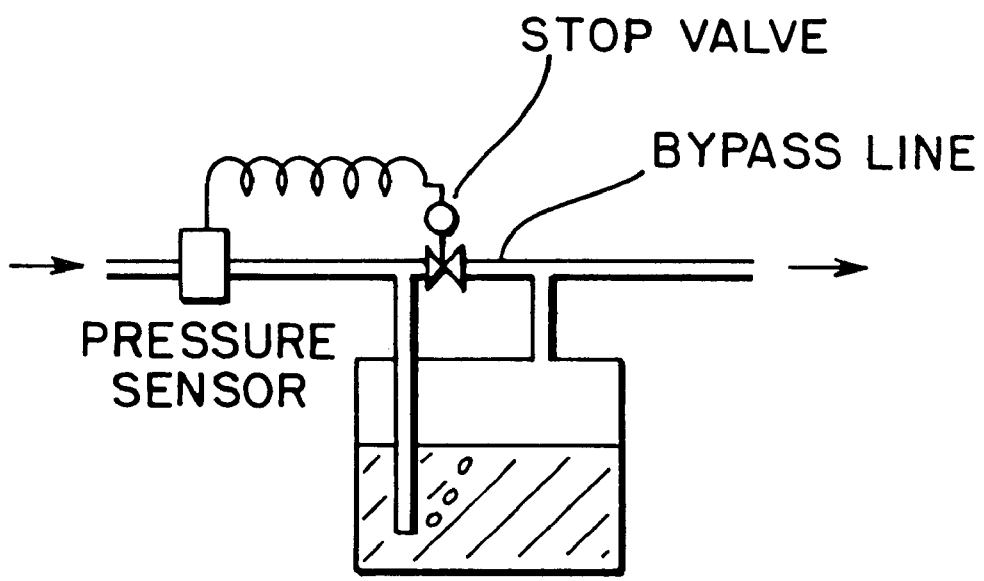
FIG. 2 is a diagram showing the oxygen analyzer of the invention having a bypass line.

In order to solve these problems, the present inventors in a first embodiment invented the above-described oxygen analyzer, which is shown schematically in FIG. 2. Pressure difference detecting means comprising a pressure sensor detects the pressure difference between the entrance and the exit of a detector and if it exceeds a specified level, a check valve is opened to equalize the two pressure levels. In the present invention, the check valve is provided in the bypass line between the entrance and the exit of the detector. During ordinary measurement, the check valve is closed, so the gas to be measured does not pass through the check valve. Therefore, the amount of the gas that need be purged out of the valve before the gas to be measured is supplied to the detector is sufficiently reduced to prevent the aforementioned problem of deteriorated response. In addition to a pressure sensor, a flow sensor may also be used as the aforementioned pressure detecting means, which may be any kind of means that is capable of detecting the pressure difference in either a direct or indirect manner.

A second embodiment of the invention relates to a method of controlling an oxygen analyzer suitable for use in the oxygen analysis of gases containing very small amounts of oxygen and it is characterized in that the oxygen analyzer has a valve on both a pipe for gas supply to a detector and a pipe at gas outlet and, when stopping the supply of a gas, closes a valve on the supply pipe immediately after closing the valve on the outlet pipe and, when resuming the supply of a gas, opens the supply pipe after opening the outlet pipe.

If the analysis is interrupted and resumed after the passage of a long time, a considerable time is taken for the result of the analysis to stabilize in the prior art. The present inventors have found that the cause of this phenomenon is the back diffusion of aerial oxygen from a pipe at the exit of the detector during shutdown. In order to prevent this back diffusion of aerial oxygen, a valve is provided on the pipe at the exit of the detector and another valve is provided on a gas supply pipe; in addition, these valves are subjected to on-off control both when the analysis is suspended and when it is resumed, whereby the diffusion and back flow of air toward the detector can be prevented at any of the times when the analysis is suspended, or as long as it is suspended, or when it is resumed, with the result that the adverse effects of the stated phenomena are eliminated.

A third embodiment of the invention relates to an oxygen analyzer suitable for use in the oxygen analysis of gases containing very small amounts of oxygen and it is characterized by having a combination valve in which a directional control valve for supplying an analyte gas to either a purifier or a detector is made integral with a check valve.

In the measurement of the concentration of trace oxygen, the presence of dead zones within the apparatus will eventually deteriorate its response. The present inventors conducted studies in order to minimize these dead zones and, as a result, they found that although several valves were conventionally used at the sites mentioned above, such valves could be integrated into a unitary assembly, thus producing satisfactory results by eliminating the pipes and joints for connecting the valves. Further, the use of such a unitary assembly of valves contributed to space saving, thereby enabling scale reduction of the apparatus.

Figure 3:
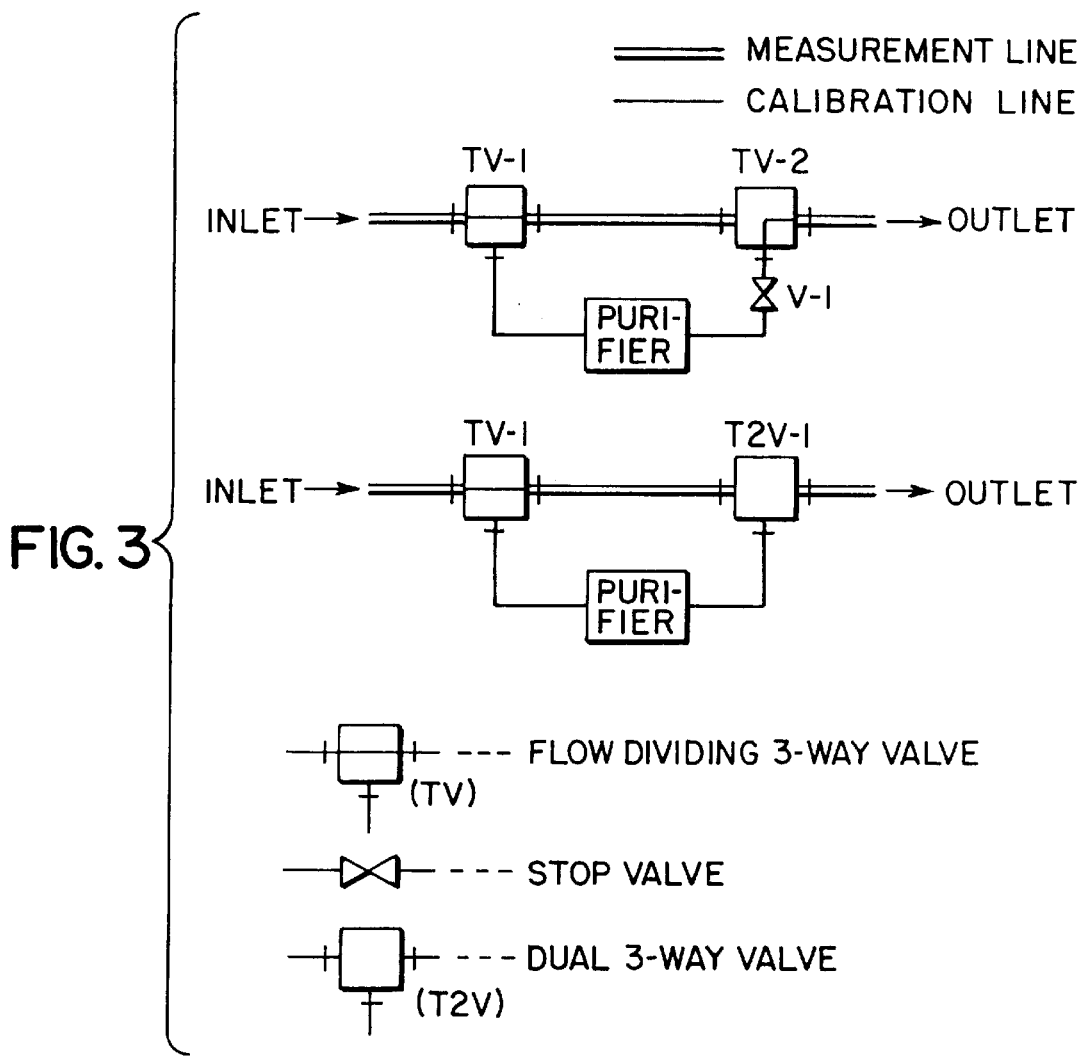
FIG. 3 is a diagram showing the line configuration of the prior art analyzer, as well as the arrangement of valves used for switching between lines.

FIG. 3 show the line configuration in a prior art analyzer and the arrangement of valves used to switch between lines. As one can see from the Figure, so many valves have been used in the prior art that dead zones occur on account of the pipes and joints necessary to connect them. Referring to FIG. 3(a), the pipe between three-way valves TV-1 and TV-2 and the pipe between three-way valve TV-2 and stop valve V-1 creates dead zones in the measurement line at the start of measurement. Referring now to FIG. 3(b), the pipe between three-way valves TV-1 and T2V-1 creates a dead zone at the start of measurement.

Figure 4:
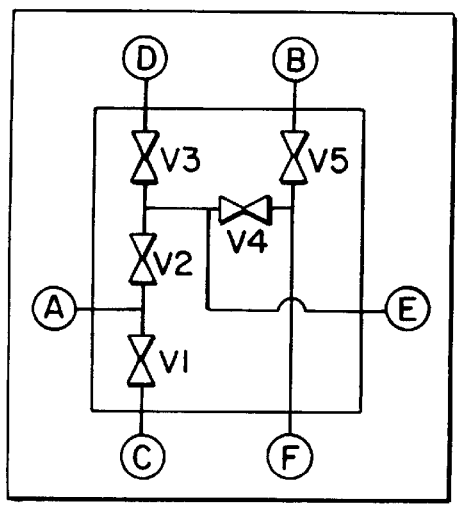
FIG. 4 shows a diagram showing the configuration of a combination valve.

FIG. 4 shows the composition of a combination valve employed in the analyzer of the invention. In the combination valve shown, A designates the inlet of the gas to be detected and B, the outlet of the gas to be detected whereas C designates the entrance of a purifier, D, the exit of the purifier, E, the entrance of a detector, and F, the exit of the detector. V4 is equivalent to the check valve shown in FIG. 2. The pressure sensor in FIG. 2 is provided near the inlet A. FIG. 4 is drawn as if pipes existed among V1–V5 for the sake of convenience in representing the passageways of a gas but, in fact, these pipes are extremely short in the combination valve and occupy so small a space that they could be described as non-existent. By employing the combination valve of this composition, it has become possible to minimize the dead zones within the apparatus and reduce its scale.

A fourth embodiment of the invention relates to a method of controlling an oxygen analyzer suitable for use in the oxygen analysis of gases containing very small amounts of oxygen and it is characterized in that the oxygen analyzer has a sensor for detecting the liquid level of a detector and an outlet valve on a water tank which is in operative association with said sensor and also characterized in that if the liquid level of the detector has become lower than a specified level, the detector is automatically replenished with water until it reaches the specified level.

During measurements, water gradually evaporates from the electrolyte in the detector, so the level of the electrolyte in the detector decreases gradually. It is therefore necessary to perform occasional replenishments with water during measurements over an extended period of time. The oxygen analyzer of the invention enables automatic replenishment with water not only to avoid human errors during the replenishing operation but also to ensure optimal conditions of analysis by supplying additional water in an appropriate manner even in unattended operations such as at night.

A fifth embodiment of the invention relates to an oxygen analyzer suitable for use in the oxygen analysis of gases containing very small amounts of oxygen and it is characterized by having a pipe arrangement in which the water in a water tank can be contacted with a gas to be measured, an effluent gas from a detector or an oxygen-free gas such that the dissolved oxygen in the water in the water tank can be eliminated.

A sixth embodiment of the invention relates to an oxygen analyzer suitable for use in the oxygen analysis of gases containing very small amounts of oxygen and it is characterized in that a pipe for supplying water from a water tank to a detector is made of an oxygen impermeable material.

The invention of the fifth and of the sixth embodiment are both intended to ensure that the results of measurements will not be affected by the dissolved oxygen in the replenishing water. Stated more specifically, the water to be additionally supplied from the tank to the detector is ensured against dissolution of oxygen by both eliminating the dissolved oxygen in the water in the tank and by preventing the dissolution of aerial oxygen via the water supply pipe. In microanalysis of oxygen, the results of analysis will be affected even by the oxygen contained in the water being additionally supplied into the detector.

In the invention of the fifth embodiment, a gas to be measured, an effluent gas from the detector or an oxygen-free gas is introduced into the water tank and bubbling or some other means is employed to have these gases contacted with the water in the tank such that the dissolved oxygen in the water is removed.

The oxygen impermeable material to be used in the invention recited in the sixth embodiment is preferably a metal. Oxygen analyzers have such a structure that their pipelines are complicated. Under the circumstances, the pipes in the prior art analyzers have been made of easily processable resins but the resins are permeable to oxygen. However, the processing technology has advanced to such an extent that it is now possible to use pipes made of metals and like materials that have heretofore been difficult to process.

Figure 5:
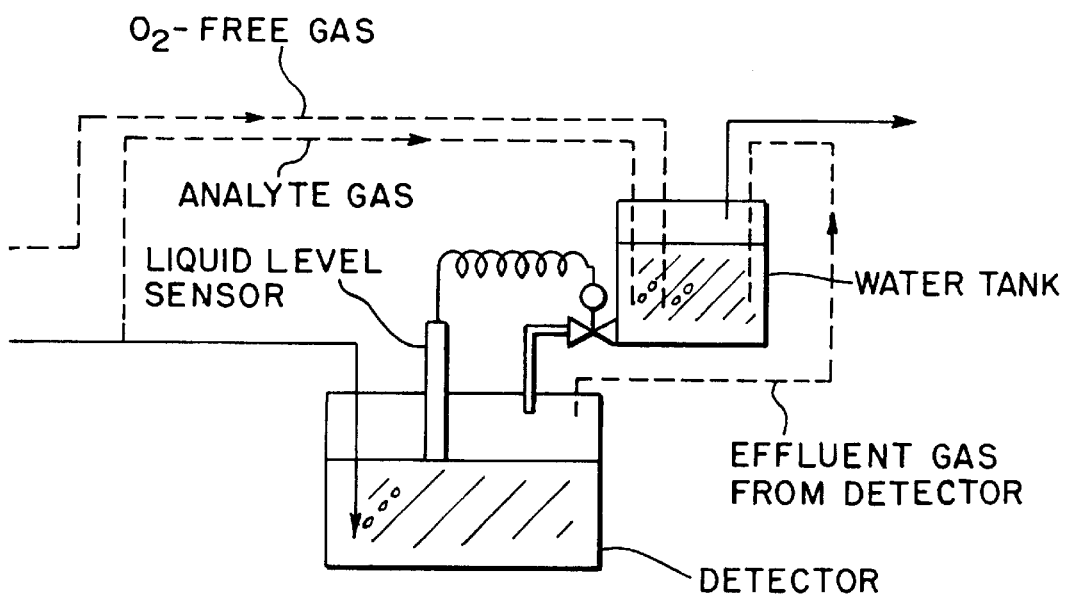
FIG. 5 is a diagram of an oxygen analyzer that has an automatic water replenisher, as well as a device for purging a water tank as with an effluent gas from a detector.

FIG. 5 shows an example of the analyzer according to the fourth, the fifth, and the sixth embodiments of the invention. The detector is fitted with a liquid level detecting sensor and a valve in operative association with the sensor is provided halfway the pipe for supplying water from the water tank to the detector. The dashed lines represent the lines in which the gas to be measured, the effluent gas from the detector and the oxygen-free gas are respectively supplied to the water tank.

The seventh embodiment of the invention relates to a method of adjusting an oxygen analyzer suitable for use in the oxygen analysis of gases containing very small amounts of oxygen and it is characterized by performing automatic zero and gain adjustments by the following operating procedure:

1) a gas to be measured is freed of oxygen with a purifier to prepare a zero gas which is supplied to the detector for measurement, which is carried out until the difference between maximal and minimal values of detection of oxygen concentration within a specified time becomes smaller than a specified value relative to full scale, thereby performing zero adjustment; and 2) said zero gas is mixed with the gas produced by electrolysis of water, thereby preparing a gas for gain adjustment, said gas being then supplied to the detector for measurement, which is carried out until the difference between maximal and minimal values of detection of oxygen concentration within a specified time becomes smaller than a specified value relative to full scale, thereby performing ain adjustment.

The prior art apparatus has not a control circuit of the type contemplated by the invention which is capable of performing automatic zero and gain adjustments and the introduction of gases, as well as the switching from one kind of gas to another have been accomplished manually; in addition, instructions are checked for stability by the operating personnel and adjusted to respective values manually. As a result, the checking for stability and the adjustment of values have involved errors between operators to cause fluctuations in adjustments. These problems have been solved by the apparatus of the invention and more reliable data are provided.

The "specified time" within which judgment is made about detected values can be determined at any desired value but it is typically about 15 minutes. The "specified value relative to full scale" against which judgment is made on stability can also be determined at any value but it is generally in the range from about ±5 to ±0.25%. Take, for example, the case of zero adjustment; the zero gas is supplied to the detector for measurement which is continued for 15 minutes; the difference between the maximal and minimal values of this 15-min detection is calculated and if it is within ±0.25% of the full scale, the detection is judged to have stabilized; if the value at that time is not zero, correction is made to insure that the detector reads "zero", whereby the process of zero adjustment is completed.

In gain adjustment, the zero gas and the gas produced by electrolysis of water are mixed to prepare a gas for gain adjustment, which is supplied to the detector for measurement. By adjusting the mixing proportions of the two gases, one can prepare a gas for gain adjustment having a desired oxygen concentration. The procedure of gain adjustment is basically the same as the procedure of zero adjustment.

We claim:

1. An oxygen analyzer of the Hersch galvanic type for detecting an oxygen concentration of 1 ppm or less in a feed gas, said analyzer comprising:

a detector comprising electrodes in a solution containing an electrolyte, whereby oxygen in a feed gas to the detector contacts the solution and undergoes a chemical reaction with one of said electrodes to form ions in the solution, the resulting ions migrating through the electrolyte solution to another of said electrodes and reacting therewith to produce an electric current between said electrodes, said current corresponding to the oxygen concentration of said feed gas;

a supply pipe having a valve to supply said feed gas to said detector;

an outlet pipe having a valve for discharging gas from said detector;

a bypass pipe extending between said supply pipe and said outlet pipe;

a check valve in said bypass pipe for regulating gas flow through said bypass pipe and preventing back flow of electrolyte into the gas supply pipe; and a detector for detecting the pressure difference between said supply pipe and said outlet pipe.

2. A method of controlling the flow of atmospheric oxygen into an oxygen analyzer of the Hersch galvanic type for analyzing an oxygen content of a feed gas having an oxygen content of 1 ppm or less, said analyzer comprising:

a detector having electrodes in a solution containing an electrolyte, whereby oxygen in said feed gas contacts the solution and undergoes a chemical reaction with one of said electrodes to form ions in the solution, the resulting ions rating through the electrolyte solution to another of said electrodes and reacting therewith to produce an electric current between said electrodes, said electric current corresponding to the oxygen content of said feed gas; a supply pipe having a valve for supplying said feed gas to said detector; and an outlet pipe in a valve for discharging gas from said detector said method comprising the steps of closing said valve on the outlet pipe and, immediately thereafter closing said valve on said supply pipe during shutdown of said analyzer to prevent back flow of atmospheric oxygen into said detector, and resuming the supply of a gas, by the steps of first opening the valve on said outlet pipe and then opening the valve on the supply pipe.

3. An oxygen analyzer of the Hersch galvanic type for analyzing a feed gas having an oxygen concentration of 1 ppm or less, said analyzer comprising:

a detector having electrodes in a solution containing an electrolyte whereby oxygen in a feed gas to the detector contacts the solution and undergoes a chemical reaction with one of said electrodes to form ions in the solution, the resulting ions migrating through the electrolyte solution to another of said electrodes and reacting therewith to produce an electric current between said electrodes, said electric current corresponding to the oxygen concentration of said feed gas;

a supply pipe for supplying said feed gas to said detector;

an outlet pipe for discharging gas from said detector; and a combination valve comprising a directional control valve for supplying an analyte gas to a purifier or to said detector and a check valve in said bypass pipe for supplying said feed gas to said detector and preventing the back flow of electrolyte into said gas supply pipe.

4. A method of controlling the water level in an oxygen analyzer of the Hersch galvanic type for analyzing an oxygen content of a feed gas having an oxygen concentration of 1 ppm or less, said analyzer comprising:

a detector having electrodes in a solution containing an electrolyte whereby oxygen in said feed gas contacts the solution and undergoes a chemical reaction with one of said electrodes to form ions in the solution, the resulting ions migrating through the electrolyte solution to another of said electrodes and reacting therewith to produce an electric current between said electrodes, said electric current corresponding to the oxygen concentration of said feed gas;

a supply pipe having a valve for supplying said feed gas to said detector;

an outlet pipe having a valve for discharging gas from said detector;

a sensor for detecting the liquid level of said electrolyte solution in said detector;

a water tank connected to said detector;

a supply pipe for supplying water from a water tank to said detector;

an outlet valve on said water tank operatively coupled to said sensor, said method comprising sensing a liquid level in said detector below a predetermined level in said detector, and activating said outlet valve to supply water from said water tank to said detector to replenish said water to said predetermined level in said detector, and closing said outlet valve upon replenishment of water to said predetermined level.

5. An oxygen analyzer of the Hersch galvanic type for analyzing the oxygen content of a feed gas having an oxygen concentration of 1 ppm or less, said analyzer comprising:

a detector comprising electrodes in a solution containing an electrolyte whereby oxygen in a feed gas to the detector contacts the solution and undergoes a chemical reaction with one of said electrodes to form ions in the solution, the resulting ions migrating through the electrolyte solution to another of said electrodes and reacting therewith to produce an electric current between said electrodes, said electric current corresponding to the oxygen concentration of said feed gas;

a supply pipe having a valve for supplying a feed gas to said detector;

an outlet pipe having a valve for discharging said gas from said detector;

a sensor for detecting the liquid level of said solution in the detector;

a water tank coupled to said detector;

a supply pipe for supplying water from said water tank to said detector;

an outlet valve on said water tank operatively associated with said sensor and being actuated by said sensor when said sensor senses a liquid level in said detector below a specified level for replenishing said detector with water to said specified level.

6. An oxygen analyzer of the Hersch galvanic type for analyzing the oxygen content of a feed gas having an oxygen concentration of 1 ppm or less, said analyzer comprising a detector comprising electrodes in a solution containing an electrolyte whereby oxygen in a feed gas to the detector contacts the solution and undergoes a chemical reaction with one of said electrodes to form ions in the solution, the resulting ions migrating through the electrolyte solution to another of said electrodes and reacting therewith to produce an electric current between said electrodes, said electric current corresponding to the oxygen concentration of said feed gas;

a supply pipe having a valve for supplying a feed gas to said detector;

an outlet pipe having a valve for discharging said gas from said detector;

a sensor for detecting electrolyte level in said detector;

a water tank connected to said detector;

an oxygen impermeable pipe for supplying water from said water tank to said detector;

an outlet valve on said water tank coupled to said sensor and being actuated when said electrolyte level in said detector is below a predetermined level.

7. A method for performing automatic zero and gain adjustments in a Hersch type oxygen analyzer comprising a detector comprising electrodes in a solution containing an electrolyte, whereby oxygen in a feed gas to the detector contacts the solution and undergoes a chemical reaction with one of said electrodes to form ions in the solution, the resulting ions migrating through the electrolyte solution to another of said electrodes and reacting therewith to produce an electric current between said electrodes, said current corresponding to the oxygen concentration of said feed gas;

a supply pipe having a valve to supply said feed gas to said detector;

an outlet pipe having a valve for discharging gas from said detector;

said method comprising the steps of freeing the gas to be measured of oxygen with a purifier to thereby prepare a zero gas and supplying the zero gas to the detector for measurement, wherein freeing of oxygen is carried out until the difference between maximal and minimal values of detection of oxygen concentration within a specified time becomes smaller than a specified value relative to a full scale, thereby performing zero adjustment; and mixing said zero gas with a gas produced by electrolysis of water thereby preparing a gas for gain adjustment, and supplying said gain gas to the detector for measurement, which is carried out until the difference between maximal and minimal valves of detection of oxygen concentration within a specified time becomes smaller than a specified value relative to full scale, thereby performing gain adjustment.

* * * * *

UNITED STATES PATENT AND TRADEMARK OFFICE
CERTIFICATE OF CORRECTION

PATENT NO : 6,024,922
DATED : February 15, 2000
INVENTOR(S) : Yoshiyasu TANAKA et al.

It is certified that error appears in the above-identified patent and that said Letters Patent are hereby corrected as shown below:

On Page 1 of the patent, line [54], correct the Title of the Invention to read:

MODIFIED OXYGEN ANALYZER OF THE HERSCH GALVANIC TYPE COMPRISING BYPASS PIPE COUPLING, CHECK VALVE, AND PRESSURE DIFFERENTIAL DETECTION MEANS, AS WELL AS METHODS OF REGULATING SAID INSTRUMENT

Signed and Sealed this

Seventeenth Day of April, 2001

*Attest:*

NICHOLAS P. GODICI

*Attesting Officer*        Acting Director of the United States Patent and Trademark Office